(12) United States Patent
Lange De Oliveira et al.

(10) Patent No.: US 9,228,985 B2
(45) Date of Patent: Jan. 5, 2016

(54) DEVICE AND METHOD FOR TESTING CATALYSTS WITH VARIABLE PROCESS PRESSURE ADJUSTMENT

(75) Inventors: Armin Lange De Oliveira, Heidelberg (DE); Michael Dejmek, Birkenau (DE); Oliver Koechel, Bubenheim (DE); Juergen Bechtel, Heidelberg (DE)

(73) Assignee: hte GmbH the high throughput experimentation company, Heidelberg (DE)

( * ) Notice: Subject to any disclaimer, the term of this patent is extended or adjusted under 35 U.S.C. 154(b) by 0 days.

(21) Appl. No.: 13/880,821

(22) PCT Filed: Oct. 17, 2011

(86) PCT No.: PCT/EP2011/005208
§ 371 (c)(1),
(2), (4) Date: Jul. 3, 2013

(87) PCT Pub. No.: WO2012/052149
PCT Pub. Date: Apr. 26, 2012

(65) Prior Publication Data
US 2013/0273662 A1    Oct. 17, 2013

(30) Foreign Application Priority Data
Oct. 22, 2010  (EP) .................................... 10013897

(51) Int. Cl.
*G01N 31/10*   (2006.01)
*B01J 19/00*   (2006.01)
*G01N 31/00*   (2006.01)

(52) U.S. Cl.
CPC ............. *G01N 31/10* (2013.01); *B01J 19/0046* (2013.01); *B01J 19/0093* (2013.01);
(Continued)

(58) Field of Classification Search
CPC ...... B01J 19/0006; C40B 30/08; C40B 30/18; G01N 31/10
USPC ............................................. 436/37; 422/68.1
See application file for complete search history.

(56) References Cited

U.S. PATENT DOCUMENTS

| 4,527,519 A * | 7/1985 | Oonaka et al. ............ 123/188.14 |
| 7,537,739 B2 * | 5/2009 | Haas et al. .................... 422/603 |

(Continued)

FOREIGN PATENT DOCUMENTS

| DE | 10 2010 050 599 | 6/2011 |
| EP | 1 273 919 | 1/2003 |

(Continued)

OTHER PUBLICATIONS
International Search Report Issued Apr. 20, 2012 in PCT/EP11/05208 Filed Oct. 17, 2011.

*Primary Examiner* — Rebecca M Fritchman
(74) *Attorney, Agent, or Firm* — Oblon, McClelland, Maier & Neustadt, L.L.P.

(57) ABSTRACT

The present invention relates to a catalysis apparatus for testing catalysts with variable process pressure adjustment over a pressure range from 0.01 millibar to 300 bar. The apparatus preferably has a plurality of reaction chambers (101, 102, . . . ) arranged in parallel, the reaction chamber outlet-side lines (211, 212, . . . ) of which are divided into two groups of sub-lines. One group of main lines (411, 412, . . . ) is operatively connected to a regulating valve (61), which is common to all of the main lines, and to an exhaust-air line (62), and the second group of secondary lines (311, 312, 313, . . . ) and switching valves (321, 322, . . . ) is operatively connected to an analysis unit (34). It is preferable for reaction chamber outlet-side lines (201, 202, . . . ) to be equipped in each case with a separate line for regulating fluid supply (211, 212, . . . ). In a preferred embodiment, the connecting points of the reaction chamber outlet-side lines (201, 202, . . . ) to the respective main lines (411, 412, . . . ) and secondary lines (311, 312, . . . ) have in each case one mixing vessel (301, 302, . . . ).

13 Claims, 5 Drawing Sheets

(52) U.S. Cl.
CPC .......... *B01J 2219/00286* (2013.01); *B01J 2219/00389* (2013.01); *B01J 2219/00391* (2013.01); *B01J 2219/00423* (2013.01); *B01J 2219/00477* (2013.01); *B01J 2219/00495* (2013.01); *B01J 2219/00585* (2013.01); *B01J 2219/00596* (2013.01); *B01J 2219/00601* (2013.01); *B01J 2219/00689* (2013.01); *B01J 2219/00707* (2013.01); *B01J 2219/00747* (2013.01); *B01J 2219/00792* (2013.01); *B01J 2219/00835* (2013.01); *B01J 2219/00869* (2013.01); *B01J 2219/00873* (2013.01); *B01J 2219/00963* (2013.01); *B01J 2219/00986* (2013.01)

(56) References Cited

U.S. PATENT DOCUMENTS

| 2004/0077102 | A1 | 4/2004 | Coute et al. |
| 2004/0109792 | A1 | 6/2004 | Karlsson et al. |
| 2005/0158865 | A1* | 7/2005 | Willson, III .............. 436/37 |
| 2006/0013743 | A1 | 1/2006 | Karlsson et al. |
| 2011/0058999 | A1* | 3/2011 | Ettireddy et al. ........ 423/213.5 |

FOREIGN PATENT DOCUMENTS

| WO | 03 095087 | 11/2003 |
| WO | 2004 052530 | 6/2004 |
| WO | 2005 063372 | 7/2005 |
| WO | 2008 055585 | 5/2008 |

* cited by examiner

DEVICE AND METHOD FOR TESTING CATALYSTS WITH VARIABLE PROCESS PRESSURE ADJUSTMENT

The invention relates to an apparatus and to a method for testing catalysts and for optimizing process conditions. By means of the apparatus according to the invention and the method according to the invention, it is possible to precisely set, and also vary in a controlled manner, the internal pressure within the individual reaction chambers. A characteristic of the apparatus according to the invention is a division of the reaction chamber outlet-side lines into two sub-groups of lines, the lines being operatively connected to regulating valves and/or switching valves.

The invention is in particular suitable for being utilized in apparatuses in which a plurality or multiplicity of reactors are arranged in parallel. The invention is thus of particular importance in the field of high-throughput research for the development of catalysts and for the optimization of process conditions.

Numerous apparatuses for parallel testing of catalysts are known from the prior art. Said apparatuses often differ in terms of their complexity, which may differ depending on the specific technical requirements.

The present invention lies, in principle, in the field of apparatus types which are equipped with a specific process control system such as is described in more detail for example in U.S. Pat. No. 7,537,739 B2. Said specific process control system is, inter alia, characterized in that the reactors arranged in parallel are equipped with a common pressure-regulating gas supply and a common pressure-holding gas supply. In this way, it is possible for a series of reactors arranged in parallel to be operated under substantially identical pressure conditions—even if significant changes in volume occur within the individual reactors during the reactions.

In EP 1 273 919 B1, Corma et al. disclose a catalysis apparatus having a plurality of reactors arranged in parallel, in which the fluid lines situated downstream of the reactors are divided into two different lines. One group of outlet lines all lead to a common tank, with a check valve being arranged in each individual outlet line. The check valves prevent pressure fluctuations, which occur for example within the tank, from being transmitted into the reaction chambers. The check valves have the effect that the individual lines and the reactors connected thereto are decoupled from one another.

It is one of the objects of the invention to provide a catalysis apparatus by means of which the process pressure adjustment can be realized in as variable a manner as possible. It is simultaneously an aim to permit the most precise possible process pressure control within the reactors and for the apparatus to have a relatively simple technical design.

The objects stated here and further objects are achieved through the provision of a catalysis apparatus for testing solid-state catalysts in a continuous process, comprising at least one reaction chamber (101), a common reactant fluid supply (01) and a reaction chamber outlet-side line (201), wherein
 (i) each reaction chamber outlet-side line is operatively connected to a main line (411) and to a secondary line (311),
 (ii) the main line (411) is operatively connected to a regulating valve (61) and an exhaust-gas line (62),
 (iii) the secondary line (311) is operatively connected to a restrictor element (331) and to an analysis unit (34).

In a preferred embodiment, the connecting line has a switching valve (321) upstream of the restrictor element (331).

In a further preferred embodiment of the apparatus according to the invention, each reaction chamber outlet-side line (201) is operatively connected to a line for regulating fluid supply (211).

In a further preferred embodiment, the connecting point of the reaction chamber outlet line (201), main line (411) and secondary line (311) comprises a mixing vessel and/or liquid-phase separator (301).

In a preferred embodiment, the main line (50) is equipped with a supply line for pressure-holding gas (50).

In a preferred embodiment, the catalysis apparatus according to the invention, having a plurality or multiplicity of reaction chambers (101, 102, . . . ) with a common reactant fluid supply (01) and with a reaction chamber outlet-side line (201, 202, . . . ), is characterized in that
 (i) each reaction chamber outlet-side line (201, 202, . . . ) is operatively connected to in each case one main line (411, 412, 413, . . . ),
 (ii) each of the main lines (411, 412, 413, . . . ) is connected to a common exhaust-gas line (62),
 (iii) each secondary line is optionally operatively connected to a dedicated switching valve (321, 322, 323, . . . ) and is operatively connected to an analysis unit (34), the individual operative connection lines between the switching valve (321, 322, 323, . . . ) and the analysis unit (34) preferably having in each case one restrictor element (331, 332, 333, . . . ) and further preferably one or more multi-port valves.

In a preferred embodiment, the apparatus according to the invention is characterized in that the connecting points of the individual reaction chamber outlet-side lines (201, 202, . . . ) to the main lines (411, 412, . . . ) and the secondary lines (311, 312, . . . ) comprise in each case one mixing vessel and/or a liquid-phase separator (301, 302, 303, . . . ).

In a preferred embodiment of the apparatus according to the invention, each individual main line has in each case one supply line (401, 402, 403, . . . ) for pressure-holding gas.

In a further preferred embodiment, each individual line of the reactant fluid supply is provided with a preferably passive restrictor element.

In a further preferred embodiment, the restrictor elements (331, 332, 333, . . . ) or (33) are micro-regulating valves. The regulating valves or micro-regulating valves must have a suitable adjustment range. A suitable adjustment range means that the adjustment range can be adapted to the prevailing pressure and the prevailing flow speed in such a way that the flow can be (relatively) varied by at least 5%.

In a further preferred embodiment, the regulating valve (61) is a high-temperature regulating valve or is composed of a cascade of regulating valves or high-temperature regulating valves.

The invention also relates to a method for testing solid-state catalysts or for optimizing process conditions by means of the catalysis apparatus according to the invention, in which method reactant fluid is conducted simultaneously through a plurality of reaction chambers (101, 102, . . . ), and the method is distinguished by
 (a) either predominant parts or all of the product fluid from each individual reaction chamber (101, 102, . . . ) being conducted entirely through the respective main line (411, 412, . . . ) via a valve (61) into the exhaust-air line (62) common to all of the main lines (411, 412, . . . ), and/or
 (b) at least a part of the product fluid of one or more reaction chambers being conducted through the secondary line (311, 312, . . . ), which is operatively connected to the respective reaction chamber, to an analysis unit or a plurality of analysis lines (34), the pressure in the individual reaction chambers being regulated by means of the regulating valve (61).

The method according to the invention is preferably characterized in that it is used for testing solid-state catalysts or for optimizing process conditions, wherein the method is carried out in a pressure range from 0 to 200 bar, preferably from 0 to 100 bar and more preferably from 0 to 30 bar, and here, the pressure can preferably be varied continuously or discontinuously within the pressure range.

The method according to the invention is characterized in that the method is carried out at a reaction chamber internal temperature in the range from 20 to 1200° C., with a temperature range from 50 to 800° C. being preferable and a temperature range from 100 to 650° C. being particularly preferable.

The present invention also relates to a computer having a computer program product—or a processor-based control unit such as for example a PLC—for controlling the catalysis apparatus according to the invention and for carrying out the method according to the invention.

BRIEF DESCRIPTION OF THE FIGURES

In FIG. 3, in each case one dedicated throttle element is provided per gas line (301, 302, ...).

Figure 1:
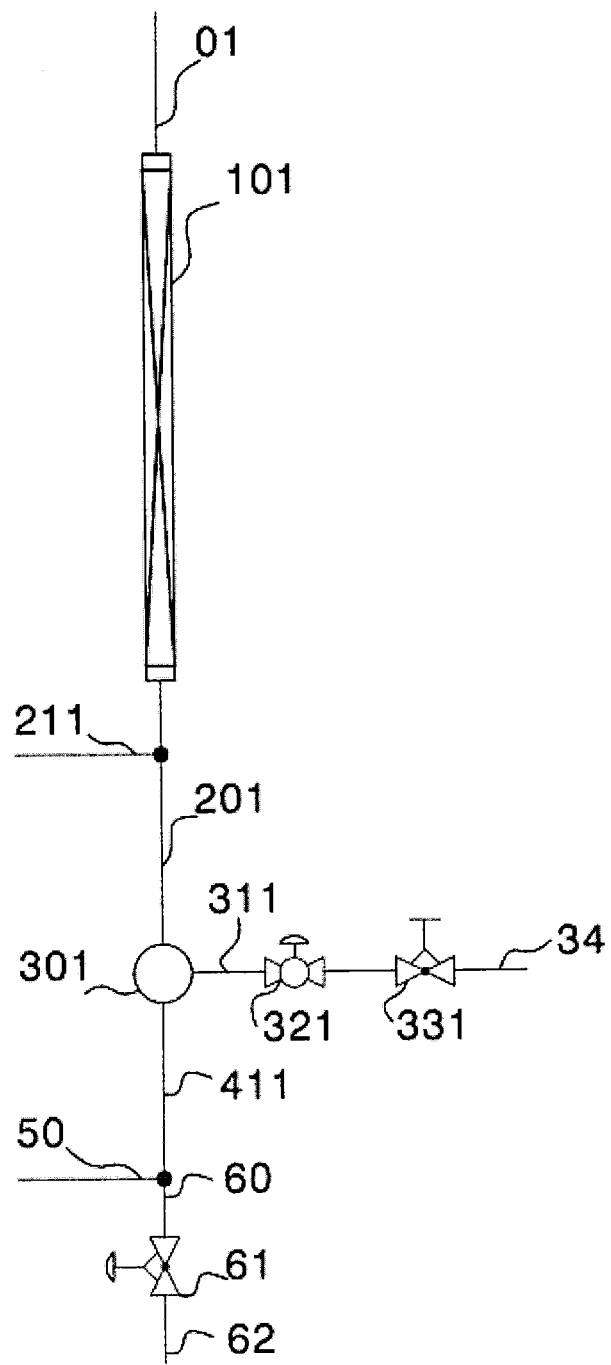
FIG. 1 is a schematic illustration of an apparatus according to the invention having a single reactor (101), in which apparatus the reaction chamber outlet-side line (201) is divided into two sub-lines (411) and (311), wherein the sub-line (411) leads to the exhaust air and the sub-line (311) leads to the analysis unit (34). The exhaust-air line (411) is provided with regulating valve (61) and the connecting line (311) to the analysis unit (34) is provided with switching valve (321) and flow limiter or restriction (331).
Figure 2:
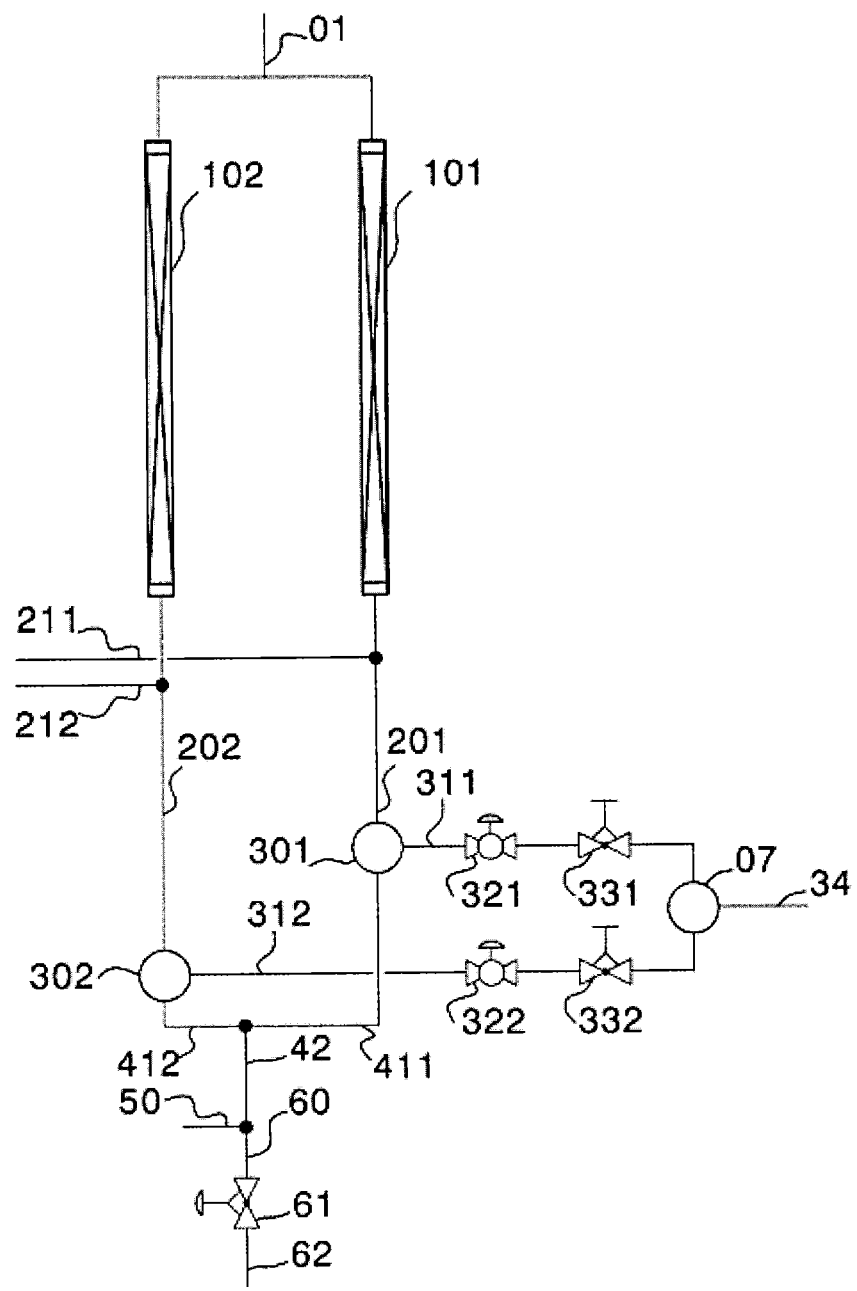
FIG. 2 is a schematic illustration of an apparatus according to the invention having two reactors (101, 102, ...) arranged in parallel, in which apparatus the reaction chamber outlet-side connecting lines (311), which are connected to the analysis unit (34), are operatively connected to a multi-port valve (07).
Figure 3:
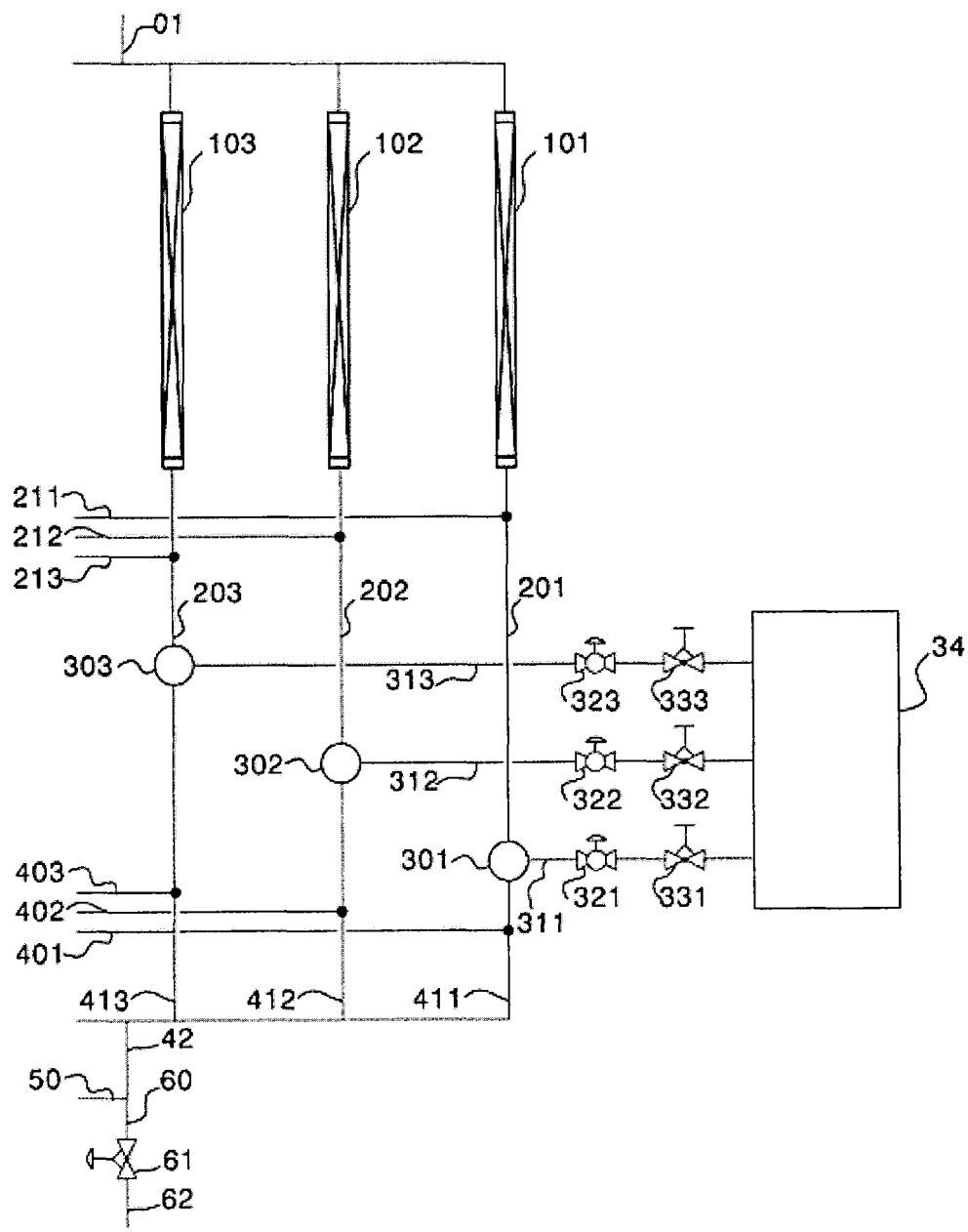
FIG. 3 is a schematic illustration of an apparatus according to the invention having three reactors (101, 102, ...) arranged in parallel, in which apparatus the reaction chamber outlet-side connecting lines lead to mixing elements (301, 302, ...) and no multi-port valve is arranged in the lines to the analysis unit (34).

Further details of the catalysis apparatuses according to the invention will be presented in the following part.

A further feature of the catalysis apparatus according to the invention is that the reaction chamber outlet-side lines (201, 202, ...) do not lead to a common damping vessel. Furthermore, it is preferable for the connecting lines between the outlet sides of the reactors and the regulating valve (61) not to have check valves.

By means of the catalysis apparatus according to the invention, it is possible for the pressure conditions in the individual reactors to be substantially constant while the catalysis experiments are carried out.

In a preferred embodiment, the catalysis apparatus according to the invention has individual line regions in which the diameter is enlarged in relation to the lines at other locations. The regions with the wider diameters and the enlarged volumes have for example the function of a mixing path, in which the pressure build-up gas and the product fluid stream are intensively mixed. Said regions will also be referred to hereinafter as mixing vessels (301, 302, ...).

A mixing vessel within the meaning of the present invention preferably has a diameter at least twice that of the line leading to the mixing vessel (301, 302, ...). It is furthermore preferable for a mixing vessel (301, 302, ...) to have at least a length to diameter ratio of two to one. It is furthermore preferable for flow-disrupting fittings to be provided in the mixing vessel, such as for example Raschig rings, grit, chips, broken granulate or packings for distillation columns. Use may also be made of fittings of corresponding nature to the distillation columns, such as for example bubble trays.

In a further preferred embodiment of the catalysis apparatus according to the invention, the individual exhaust-gas lines (311, 312, ...) which lead to the analysis unit (34) are connected directly to the respective mixing vessels (301, 302, ...). It is achieved in this way that a very well-mixed sample can be extracted from the product fluid stream emerging in each case from the reactor.

The necessary provisions for sample mixing are dependent on the respective product spectrum and the process parameters with which the apparatus according to the invention is operated.

In a preferred embodiment, the apparatus according to the invention is operated as a gas-phase apparatus, which means that reactant fluids present predominantly in the gaseous state are converted to predominantly gaseous product fluids.

If the catalysis apparatus is used for processes in which the product fluid stream also comprises liquid constituents or constituents that may condense out under the prevailing reaction conditions, the mixing vessel or the mixing vessels (301, 302, ...) may also, in addition to the mere mixing function, have the function of a separator or of a collecting vessel (or of collecting vessels) for liquid samples.

The exhaust-gas lines (311, 312, ...) leading to the analysis unit are preferably connected to the mixing vessels or separators in such a way that substantially only gaseous product fluid is extracted from the separators.

In a further preferred embodiment, the mixing vessel or separator has the function of a damping vessel which ensures that the pressure in the interior of lines and reactors does not vary, or varies only slightly, during the extraction of gas. The extraction of gas takes place via the exhaust-gas lines (311, 312, ...) and serves for the supply of analysis gas to the analysis unit.

In a further embodiment of the catalysis apparatus according to the invention, liquid samples may also be extracted from the separator or the separators. This may be realized optionally by means of a common discharge valve for liquid and gaseous samples or by means of two separate discharge valves. In the latter case, the discharge valve for liquid samples acts preferably at the base of the mixing vessel or separator. The action at the base is realized by virtue of the valve being situated on the lower part of the vessel or by virtue of said valve being connected to an ascending pipe in the interior of the vessel. By contrast, the discharge valve for the gaseous sample extracts the gaseous sample from the gas chamber of the mixing vessel or separator in the exhaust flow.

With regard to the throttling elements (331, 332, 333, ... ) in the exhaust lines, it is preferable for said throttling elements to be passive or active restrictor elements. Control is thus realized by means of the passive restrictor elements or by means of active restrictor elements set to a constant value.

By contrast, it is also possible for a regulating circuit to be integrated in this plant region. This is realized in that one or more flow sensors are provided upstream or downstream of throttle elements or actuating elements (331, 332, ... ), said flow sensors acting on the element (33). The flow sensor is preferably a mass flow sensor or a volume flow sensor.

The embodiment of the apparatus according to the invention is ultimately dependent also on the operating state in which the catalysis apparatus according to the invention is operated. As passive restrictor elements, use may for example be made of capillaries, perforated screens, micro-ducts or porous chips. The active throttle elements are preferably micro-valves (fine-regulation needle valves), mass through-flow regulators or else automated fine-regulation valves. The automated fine-regulation valves may be for example ReCO valves from the company Badger-Meter.

Figure 4:
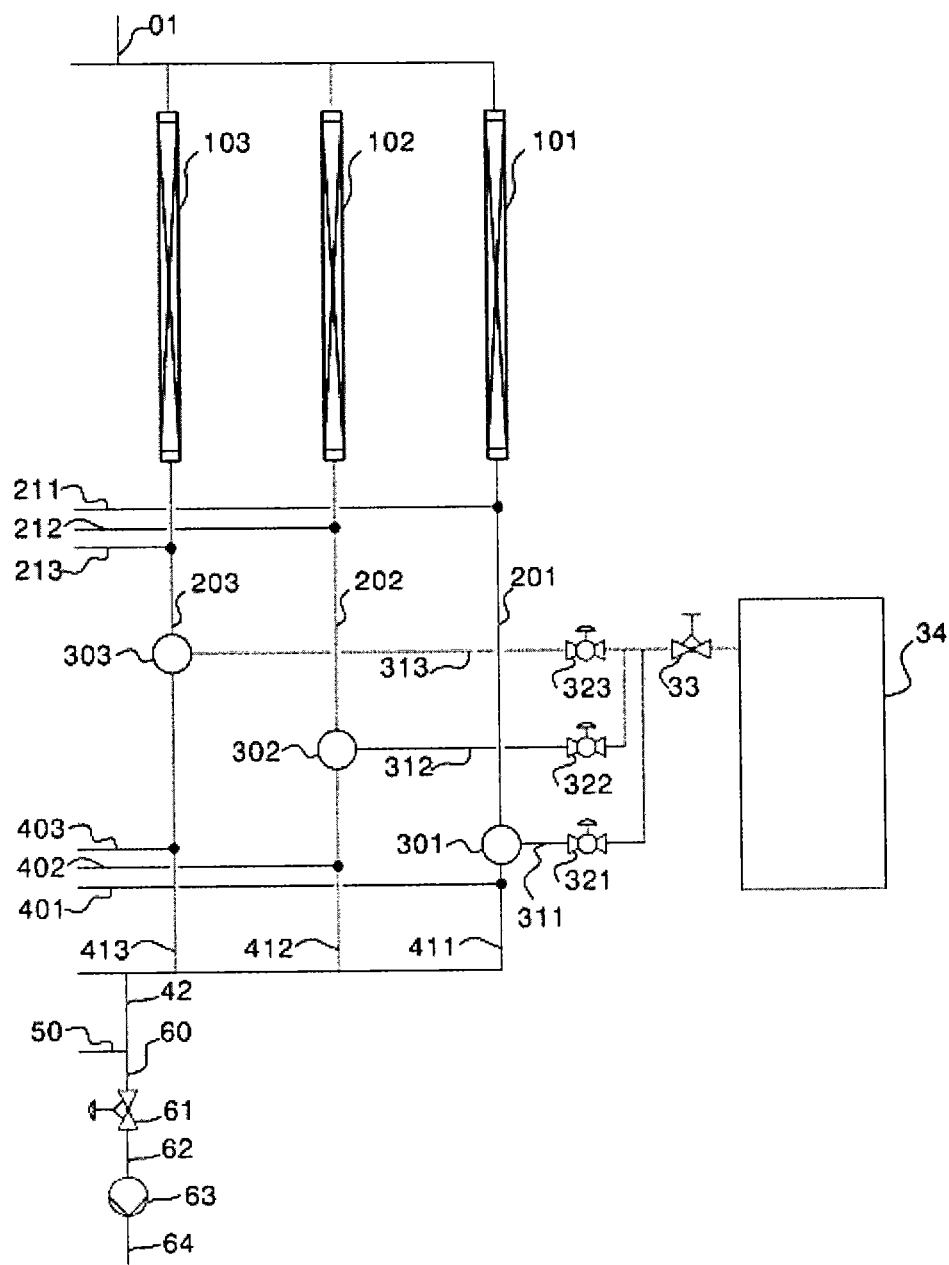
FIG. 4 is a schematic illustration of an apparatus according to the invention having three reactors (101, 102, ...) arranged in parallel, said apparatus corresponding to the apparatus shown in FIG. 3, wherein the outlet lines (311, 312, 313) for the gaseous connections are led via a single flow regulator or via a single throttle element (33).

If the apparatus has a hot-gas analyzer as an analysis unit, it is possible for both the amount of extracted gas sample and also the composition to be detected. It is also possible for a precise quantitative detection to take place by virtue of the signal of the hot-gas flow meter being corrected by the gas composition determined by means of the hot-gas analyzer. Here, it must be ensured that the entire product gas stream from the respective reactor is extracted in order to determine an absolute flow rate. This however also requires a separate supply of pressure-holding gas or of additional pressure build-up gas into each individual exhaust-gas line (see FIG. 4, lines 401, 402, ... ).

In a further embodiment, there is dosed into the fluid streams a predefined amount of reference gas, which constitutes an internal standard and makes it possible to quantitatively detect the recovery rate of carrier gas or of pressure build-up gas. This internal standard may be for example a certain fraction of argon gas. Owing to the addition of a standard, it is not necessary to quantitatively detect the amount conveyed through the outlet lines (311, 312, ... ) to the analysis unit. This can be advantageous because, in this way, the measurement and regulation outlay that would otherwise be required for the quantitative detection of the gas streams and the associated balancing of the reaction can be reduced.

The quantitative detection is then performed by means of the analysis of the gas stream. For example, in the case of argon gas being used as an internal standard, a gas chromatograph is used as an analysis unit, said gas chromatograph being equipped with a thermal conductivity or helium ionization detector which reacts sensitively to argon. In the case of other fluids which serve as an internal standard, other analytical methods are applied correspondingly. The configuration, disclosed here, of a combination of a GC detector which is used with argon gas as a standard or tracer gas is specified here by way of example. Any other possible combination of internal standard and a substance-specific detector may likewise be used.

The main stream and the product fluid are supplied via a common regulating valve (61) to the exhaust air. Through suitable control of the regulating valve (61) and of the back pressure regulator for the pressure-holding gas (dosed via line 50), the pressure can be controlled efficiently within the catalysis apparatus and within the individual reaction chambers. It is emphasized here as being an advantage of the method and of the apparatus of the present invention that, in the present case, the pressure can be regulated over a broader range than is possible with catalysis apparatuses known from the prior art—such as for example in U.S. Pat. No. 7,537,739 B2.

The passive restrictors disclosed in U.S. Pat. No. 7,537,739 B2 are fixed with regard to flow resistance, such that a minimum pressure is fixedly defined by the feed gas and a maximum pressure is fixedly defined by the permitted dilution of the feed gas with pressure-holding gas.

In the apparatus according to the invention, the individual exhaust-gas lines (411, 412, 413, ... ) are merged into line (42), wherein the line (42) has a regulating valve (61) which has a variable flow resistance. The variable regulating valve (61) performs the function of the restrictors arranged in parallel which—in the embodiment according to U.S. Pat. No. 7,537,739 B2—have a fixed flow resistance.

By means of the apparatus according to the invention, continuous pressure regulation is possible over a range from a few millibar up to several hundred bar even without modification of the apparatus and the use of additional functional elements. To achieve target pressures that lie below atmospheric pressure, a vacuum pump (63) must be provided, as is illustrated for example in FIG. 4.

It is emphasized that, in those embodiments of the apparatus according to the invention that are provided with a regulating fluid supply, the regulating fluid does not have a pressure regulating function. The apparatus according to the invention thus differs in this aspect from the apparatuses disclosed in WO 2005/063372 A2.

The configuration of the regulating valve (61) is based on the respective use of the catalysis apparatus and is not subject to any restriction here. If the catalysis apparatus is connected to a large number of reactors, then it is possible, and in this case preferable, for a plurality of regulating valves (61) to be arranged in parallel and for that valve which has the conductance adjustment range suited to the present pressure regime to be activated, or for a group of adjustment valves to be activated simultaneously, because in this way the pressure regulating range can be additionally expanded in a simple manner.

Figure 5:
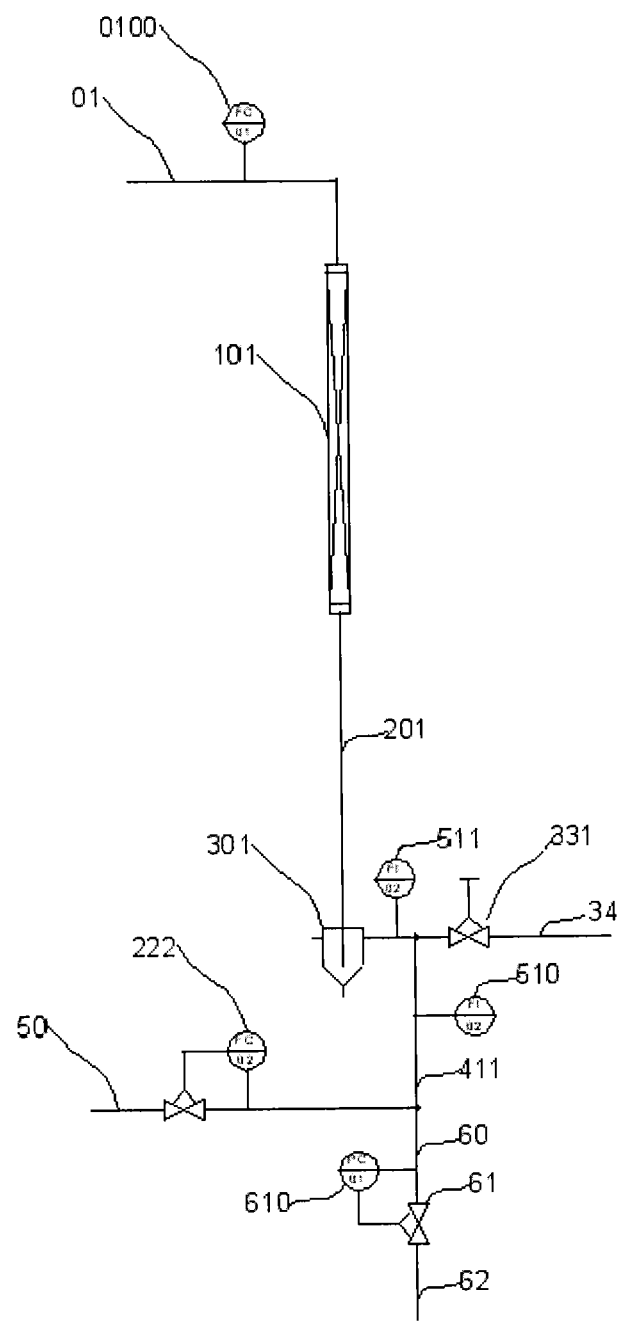
FIG. 5 is a schematic illustration of the apparatus according to the invention which is equipped with a single reactor (101), wherein the illustration also shows the regulating devices for flow and pressure control. The apparatus shown in the illustration is equipped with a pressure-holding gas supply. The pressure-regulating fluid supply is not provided in this embodiment.

It is an essential feature of the apparatus according to the invention that the apparatus is provided with a pressure regulator. It is preferable for the regulating valve (61) to be activated by a pressure regulator. Here, the reaction chamber outlet-side line region is operatively connected to a pressure sensor, wherein the regulator determines its actual value on the basis of said pressure sensor. An example of such an arrangement is illustrated in FIG. 5. Since the line with the regulating valve (61) is a main line, the pressure regulation in this embodiment of the apparatus takes place via the main line. In a preferred embodiment, the pressure regulator obtains its actual value from the line (42) or from the lines (411, 412, 413, ... ).

In a further and preferred embodiment, it is also possible for the pressure regulator to be arranged in a secondary flow line. In this case, the pressure regulator acts on the adjustment valve in the pressure-holding gas line. For the pressure regulation, it is crucial that the pressure regulator receives from the system values which as far as possible have not been changed by interference effects.

In a specific embodiment of the apparatus according to the invention, it is possible for one or more switchable restrictor elements to be connected in parallel with the line portion with the variable restrictor element (331). Here, the connection is realized by means of valves. The activation of restrictor elements has the advantage that the adjustment range of the variable restrictor element (331) can be adapted in a stepped manner to the experimental conditions, wherein this may preferably also take place in an automated fashion. Similarly, the adjustment range of the regulating valve (61) can be adapted by means of the parallel connection of restrictor elements by means of valves.

The selection of the sample extraction valve is based on the respective application. It is possible for the regulating valves to be used in exhaust-gas streams whose temperature lies in a range from 500 to 600° C. At the same time, it is possible for the pressures within the catalysis apparatus and within the individual reactors to vary over a very wide range.

If the temperatures of the product fluid streams lie in a temperature range from 500 to 600° C., then it is possible for sensitive components of the apparatus to be subjected to very high temperature loading. The apparatus according to the invention thus also offers the advantage that the main part of the volume flow can be conducted via the lines with the regulating valve (61). The regulating valve is designed so as to be particularly suitable for high-temperature operation. A small part of the volume flow is conducted via the outlet lines (311, 312, 313, . . . ), whereby the components (321, 322, 323, . . . ) are subjected to lower thermal loading.

The direct extraction of the product fluid stream also has the advantage over U.S. Pat. No. 7,537,739 B2 that the sample is not diluted by pressure-holding gas, such that the optimization of the sample analysis can be performed in the range of the actual composition of the product fluid stream, and it is not necessary to take into consideration any dilution effects (reduction of the detection limit, etc.).

The apparatus according to the invention is preferably used for the testing of catalysts in laboratories or on the pilot-plant scale. The catalysts used for the tests are preferably present in solid form, and the intake capacity of the individual reaction chamber is preferably 0.1 g to 100 g of catalyst, it being further preferable for the intake capacity of the single reaction chamber to be 1 g to 50 g. The volume of the individual reaction chamber is preferably in a range from 0.1 ml to 150 ml, particularly preferably in a range from 1 ml to 100 ml and very particularly preferably in a range from 5 ml to 50 ml.

The GHSV used for the tests preferably lies in a range from 300 to 10,000 $hr^{-1}$, preferably 500 to 3000 $hr^{-1}$, whereas the LHSV lies in a range from 0.2 to 20 $hr^{-1}$, preferably 0.5 to 10 $hr^{-1}$.

The apparatus according to the invention can be operated in a pressure range from 0.01 bar to 200 bar, the apparatus according to the invention preferably being operated in a pressure range from 0.1 bar to 100 bar. (The pressure values specified here relate to the absolute pressures prevailing in the interior of the reaction chambers.) The apparatus can preferably be used for testing reactions which lie in a temperature range from 20° C. to 1200° C., preferably from 50° C. to 800° C., with a temperature range from 100° C. to 650° C. being particularly preferable.

LIST OF REFERENCE NUMERALS

01—Reactant supply
101, 102, . . . —Reaction chambers
201, 202, . . . —Reaction chamber outlet-side lines
211, 212, . . . —Regulating fluid supply (dilution & internal standard)
301, 302, . . . —Mixing vessel
311, 312—Second sub-group of reaction chamber outlet-side lines
321, 322, . . . —Switching valve
33, 331, 332, . . . —Flow regulators or throttle elements
34—Analysis unit
401, 402, . . . —Optional additional regulating fluid supply
411, 412, . . . —First sub-group of reaction chamber outlet-side lines
30—Connecting line or transfer line between
62 and 64—Exhaust air
63—Pump
61—Regulating valve
42 and 60—Common exhaust-air line
50—Holding-gas supply
07—Multi-port valve
222—Flow regulator of the holding gas
510, 511—Flow meter for the substance balancing
34—Line to the analysis unit
610—Pressure regulator which actuates valve (61)

The invention claimed is:

1. A catalysis apparatus, comprising:
a plurality of reaction chambers, wherein each reaction chamber is directly connected to a common reactant fluid supply line and comprises a corresponding reaction chamber outlet-side line, and
a common reactant fluid supply connected to the common reactant fluid supply line,
wherein each reaction chamber outlet-side line is operatively connected to a corresponding main line which in turn is connected to a corresponding secondary line,
wherein each main line is operatively connected to a common regulating valve and a common exhaust-airline which both are located downstream of the plurality of the reaction chambers, wherein the common regulating valve and the common exhaust-airline are located downstream of the plurality of the reaction chamber, wherein the connection of each main line to the common regulating valve and the common exhaust-gas line is via the common exhaust-air line, and wherein the downstream side of the common regulating valve is in communication with the common exhaust-air line
wherein each secondary line is operatively connected to a corresponding restrictor element and to a common analysis unit, wherein each restrictor element is a high-temperature regulating valve or comprises a cascade of regulating valves or high-temperature regulating valves,
wherein the common regulating valve is a high-temperature regulating valve or comprises a cascade of regulating valves or high-temperature regulating valves,
wherein a connecting line between each main line and corresponding secondary line is equipped with a cascaded series of a switching valve and of the restrictor element guiding fluids to a multi-port valve or the restrictor element and downstream of the multi-port valve or the restrictor element to the common analytical device,
optionally, mixing vessel, and
optionally, a vacuum pump, and
the apparatus is suitable for testing solid state catalysts in a continuous process.

2. The catalysis apparatus according to claim 1, wherein a connecting point of each reaction chamber outlet-side line to a corresponding main line and a corresponding secondary line comprises a mixing vessel, a liquid-phase separator, or both.

3. The catalysis apparatus according to claim 1, wherein each reaction chamber outlet-side line comprises a supply line suitable for pressure-holding gas.

4. The catalysis apparatus according to claim 1, wherein the restrictor element is a micro-regulating valve.

5. A method for testing solid-state catalysts or for optimizing process conditions with the catalysis apparatus according to claim 1, the method comprising:
conducting method reactant fluid simultaneously through the plurality of reaction chambers in the apparatus, thereby obtaining a product fluid, and either
conducting at least a predominant part of the product fluid from each reaction chamber entirely through the respective main line via a valve into the exhaust-gas line common to all main lines, or
conducting at least a part of the product fluid of one or more reaction chambers through the secondary line, which is operatively connected to the reaction chamber, to an analysis unit or a plurality of analysis lines, and regulating pressure in each reaction chamber with the regulating valve.

6. The method according to claim 5,
wherein a pressure range of the method is from 0 to 200 bar, and
the method optionally further comprises varying the pressure continuously or discontinuously within the pressure range.

7. The method according to claim 5, wherein a reaction chamber internal temperature of the method is from 20 to 1200° C.

8. A computer having a computer program product capable of controlling the catalysis apparatus according to claim 1.

9. The method of claim 7, wherein the reaction chamber internal temperature of the method is from 50 to 800° C.

10. The method of claim 6, wherein the pressure range of the method is from 0 to 100 bar.

11. The catalysis apparatus according to claim 1, wherein the apparatus is provided with a pressure regulator.

12. The catalysis apparatus according to claim 1, wherein pressure is controlled within individual reaction chambers.

13. A catalysis apparatus, comprising:
a plurality of reaction chambers, wherein each reaction chamber is directly connected to a common reactant fluid supply line and comprises a corresponding reaction chamber outlet-side line, and
a common reactant fluid supply connected to the common reactant fluid supply line,
wherein each reaction chamber outlet-side line is operatively connected to a corresponding main line which in turn branches into secondary lines and tertiary lines,
wherein each tertiary line combines into a main line, which is operatively connected to a common regulating valve and a common exhaust-airline which both are located downstream of the plurality of the reaction chambers,
wherein the common regulating valve and the common exhaust-airline are located downstream of the plurality of the reaction chamber, wherein the connection of each main line to the common regulating valve and the common exhaust-gas line is via the common exhaust-air line, and wherein the downstream side of the common regulating valve is in communication with the common exhaust-air line, wherein the outside of the exhaust air line may be optionally connected to the inlet of a vacuum pump,
wherein each secondary line is operatively connected to a corresponding restrictor element and to a common analysis unit, wherein each restrictor element is a high-temperature regulating valve or comprises a cascade of regulating valves or high-temperature regulating valves,
wherein the common regulating valve is a high-temperature regulating valve or comprises a cascade of regulating valves or high-temperature regulating valves,
wherein a connecting line between each main line and corresponding secondary line is equipped with a cascaded series of a switching valve and of the restrictor element guiding fluids to a multi-port valve or the restrictor element and downstream of the multi-port valve or the restrictor element to the common analytical device,
optionally, the branching takes place at the connecting ports of a mixing vessel, and
the apparatus is suitable for testing solid state catalysts in a continuous process.

* * * * *